(12) United States Patent
Lozonschi

(10) Patent No.: US 10,568,740 B2
(45) Date of Patent: Feb. 25, 2020

(54) DEVICE AND METHOD TO PLICATE THE TRICUSPID VALVE

(71) Applicant: VDYNE, LLC, Dallas, TX (US)

(72) Inventor: Lucian Lozonschi, Sullivan's Island, SC (US)

(73) Assignee: VDYNE, LLC, Maple Grove, MN (US)

( * ) Notice: Subject to any disclaimer, the term of this patent is extended or adjusted under 35 U.S.C. 154(b) by 188 days.

(21) Appl. No.: 15/871,085

(22) Filed: Jan. 15, 2018

(65) Prior Publication Data
US 2019/0216602 A1 Jul. 18, 2019

(51) Int. Cl.
*A61F 2/24* (2006.01)
*A61B 17/04* (2006.01)
*A61B 17/00* (2006.01)
*A61B 17/122* (2006.01)
*A61B 17/128* (2006.01)

(52) U.S. Cl.
CPC ...... *A61F 2/2463* (2013.01); *A61B 17/00234* (2013.01); *A61B 17/0401* (2013.01); *A61B 17/122* (2013.01); *A61B 17/1285* (2013.01); *A61B 2017/00243* (2013.01); *A61B 2017/00473* (2013.01); *A61B 2017/00783* (2013.01); *A61B 2017/0414* (2013.01); *A61B 2017/0464* (2013.01)

(58) Field of Classification Search
CPC ........ A61F 2/24; A61F 2/2454; A61F 2/2457; A61F 2/2463; A61B 17/1285; A61B 17/00234; A61B 17/0401; A61B 17/122; A61B 2017/00243
See application file for complete search history.

(56) References Cited

U.S. PATENT DOCUMENTS

| | | | |
|---|---|---|---|
| 2004/0220593 A1* | 11/2004 | Greenhalgh | .......... A61F 2/2454 606/151 |
| 2016/0287387 A1* | 10/2016 | Wei | ...................... A61B 17/083 |
| 2018/0021134 A1* | 1/2018 | McNiven | .............. A61F 2/2436 623/2.11 |

* cited by examiner

*Primary Examiner* — Katherine M Rodjom
(74) *Attorney, Agent, or Firm* — Juneau & Mitchell; Todd L. Juneau

(57) ABSTRACT

The invention relates to methods and devices for plicating the tricuspid valve leaflets to bicuspidize the valve.

12 Claims, 19 Drawing Sheets

Healthy TV

Deformed TV (TVR)

Switch to Annulus

Twist

Anchor

DEVICE AND METHOD TO PLICATE THE TRICUSPID VALVE

CROSS-REFERENCE TO RELATED APPLICATIONS

Provided by Application Data Sheet in accordance with USPTO rules.

STATEMENT REGARDING FEDERALLY SPONSORED R&D

Provided by Application Data Sheet in accordance with USPTO rules.

NAMES OF PARTIES TO JOINT RESEARCH AGREEMENT

Provided by Application Data Sheet in accordance with USPTO rules.

REFERENCE TO SEQUENCE LISTING

Provided by Application Data Sheet in accordance with USPTO rules.

STATEMENT RE PRIOR DISCLOSURES

Provided by Application Data Sheet in accordance with USPTO rules.

BACKGROUND OF THE INVENTION

Field of the Invention

The invention relates to a medical prosthesis (Class 623), and in particular a clip for plicating the posterior leaflet complex of tissue, including methods for reducing the annular size of a tricuspid valve in a heart by mounting a clip or tissue anchor onto the posterior leaflet complex of tissue (leaflet, annulsu, chordae) to bicuspidize the triscuspid valve.

Description of the Related Art

Tricuspid valve regurgitation occurs when the tricuspid valve leaflets do not close, coapt, properly during systole. Systole is the contractive phase of the heart and diastole is the filling phase. When the right ventricle is contracting and pumping blood to the lungs, the right atrium is filling, and the tricuspid valve in healthy individuals is closed. When a patient has heart disease or damage, a condition can occur called right ventricular dilatation, which when the right ventricle moves outwardly away from the septal wall, i.e. to the left when viewed from the front of a patient. As a consequence of right ventricular dilatation (RVD), the tricuspid valve leaflets become deformed from their normal positions, and the valve does not close completely, causing blood that is pumped during ventricular systole to be partially ejected back into the right atrium: regurgitation.

Efforts to treat tricuspid regurgitation have included deploying a tricuspid prosthetic valve substitute. However, prosthetic tricuspid valves have at least the same type and degree of complications as in the aortic and the mitral positions, namely an increased incidence of thrombo-embolic phenomena, mechanical degeneration, valve dysfunction from tissue ingrowth. Only about 35-45% of the patients were alive free from reoperation after tricuspid valve replacement.

Another effort, DeVega, developed a procedure which consists of folding and stitching, also called "plication", of the posterior and anterior portion of the annulus, preserving the septal portion, with a double continuous suture. However, the sutures may pull out of the tissues, a phenomena called dehiscence. A variation of this procedure is to use a clip (Trialign®) to grab and cinch all three leaflets with an implanted, free-floating, permanent clip. The use of Teflon pledgets in each bite of the suture has reduced the incidence of tissue rupture, and the use of polyester fabric covering to promote tissue in-growth for the clip reduces the incidence of leaflet tearing and rupture, but both of these can cause the valve to become stenotic. Also, there is a large risk of device detachment when using surgical anchors on tissue that is as delicate and thin as the tricuspid leaflets.

Another effort to treat tricuspid regurgitation includes deployment of an annuloplasty ring. An annuloplasty ring is a rigid, horse-shoe shaped ring that is sewn onto the fibrous tissue at the top edge of the tricuspid valve, effectively mechanically forcing the valve annulus back to a crown shape so that, in theory, the leaflets hanging below the annulus will again coapt. The ring cannot be a complete circle since there exists a section of the fibrous annular tissue that is involved in electrical conductivity, called the atrio-ventricular node (AV node), which is within a highly sensitive section of tissue called the "Triangle of Koch". This section of the tricuspid annulus, above the septal leaflet, is known by surgeons and practitioners as a section that must be surgically avoided since interventions there are known to disrupt heart function. However, deployment of an annuloplasty ring is an open heart surgical procedure and therefore includes all of the attendant problems of open heart surgery, such as infection, recovery from traumatic opening of the chest wall, embolism, problems associated with use of a heart-lung bypass machine, age-related and condition-related appropriateness of invasive surgery, and other complications.

Accordingly, there exists a need for percutaneous tricuspid valve repair that addresses one or more of the problems in the prior art.

BRIEF SUMMARY OF THE INVENTION

In a preferred embodiment, the inventive subject provided herein by detailed description and as claimed is, in a preferred embodiment, a method for percutaneously anchoring tissue within a heart of a patient comprising the steps of: (i) advancing a plication clip through a lumen of a delivery catheter deployed in a right atrium of the heart of the patient to a tissue location on a posterior leaflet complex of a tricuspid valve, wherein the posterior leaflet complex comprises one or more tissues elected from tricuspid posterior leaflet tissue, triscuspid posterior annulus tissue, and tricuspid posterior leaflet chordae tendinae; (ii) deploying the plication clip onto the posterior leaflet complex by actuating the plication clip from an open position to a closed position, where the plication clip comprises a connector element and at least two elongate clip arms, a first elongate clip arm attached at a proximal end to the connector element and a second elongate clip arm attached at a proximal end to the connector element at a proximal end; wherein the open position of the deployed plication clip positions the first elongate clip arm behind the posterior leaflet in a space between the posterior leaflet and a right ventricular wall, and wherein the open position of the deployed plication clip positions the second elongate clip arm in front of the posterior leaflet in a space between the posterior leaflet and a central axial space of the tricuspid valve, and wherein the closed position of the deployed plication clip captures the posterior leaflet securely between the first and second elongate clip arms; (iii) actuating the closed plication clip to reduce annular diameter of the tricuspid valve, wherein actuating the closed plication clip deforms the posterior leaflet complex and reduces annular distance between a postero-septal commissure and an antero-posterior commissure of the tricuspid valve; and (iv) securing in place the deformed posterior leaflet complex.

In another preferred embodiment of the inventive subject matter, the method includes wherein the step of securing comprises fastening the first elongate clip arm to the second elongate clip arm using a fastener selected from a sheath, a clip suture, a tissue suture, and a second clip, where the sheath includes a lock structure for securably engaging the first and second elongate clip arms, wherein the clip suture connects a distal end of the first elongate clip arm to a distal end of the second elongate clip arm, wherein the tissue suture connects the posterior leaflet complex to a distal end of at least one of the at least two elongate clip arms, and wherein the second clip is securably mounted onto the plication clip.

In another preferred embodiment of the inventive subject matter, the method includes wherein the plication clip comprises a third elongate clip arm attached to the connector element.

In another preferred embodiment of the inventive subject matter, the method includes wherein the plication clip comprises a tissue hook for capturing the posterior leaflet complex and disposing the posterior leaflet complex within the open position of the at least two elongate clip arms.

In another preferred embodiment of the inventive subject matter, the method includes wherein the two elongate clip arms each comprise a check knob structure at a distal end.

In another preferred embodiment of the inventive subject matter, the method includes wherein at least one of the two elongate clip arms is configured to bend into a hook shape.

In another preferred embodiment of the inventive subject matter, the method includes wherein the connector element comprises one or more access ports for a catheter delivered positioning tool, and wherein the positioning tool engages one or more control wires disposed within the at least two elongate clip arms to actuate the plication clip to a closed position, to an open position, and to lock the plication clip in a closed position.

In another preferred embodiment of the inventive subject matter, the method includes wherein the at least two elongate clip arms are at least partially covered with fabric.

In another preferred embodiment of the inventive subject matter, the method includes wherein the step of actuating the plication clip comprises rotating the deployed plication clip that has captured the posterior leaflet complex.

In another preferred embodiment of the inventive subject matter, the method further comprises the step of tethering the plication clip to a moderator band within the right ventricle.

In yet another aspect or preferred embodiment of the invention, a device for percutaneously anchoring tissue within a heart of a patient is provided, comprising a plication clip comprising a connector element and at least two elongate clip arms, a first elongate clip arm attached at a proximal end to the connector element and a second elongate clip arm attached at a proximal end to the connector element at a proximal end, wherein the two elongate clip arms each comprise a check knob structure at a distal end, wherein the connector element comprises one or more access ports for a catheter delivered positioning tool, and wherein the positioning tool engages one or more control wires disposed within the at least two elongate clip arms to actuate the plication clip to a closed position, to an open position, and to lock the plication clip in a closed position, wherein the plication clip has a outer diameter in a closed position ranging from 5 Fr to 22 Fr (1.66 mm to 7.33 mm) for catheter delivery.

In yet another aspect or preferred embodiment of the invention, a system for percutaneously anchoring tissue within a heart of a patient is provided, comprising: (i) a device for percutaneously anchoring tissue within a heart of a patient, comprising a plication clip comprising a connector element and at least two elongate clip arms, a first elongate clip arm attached at a proximal end to the connector element and a second elongate clip arm attached at a proximal end to the connector element at a proximal end, wherein the two elongate clip arms each comprise a check knob structure at a distal end, wherein the connector element comprises one or more access ports for a catheter delivered positioning tool, and wherein the positioning tool engages one or more control wires disposed within the at least two elongate clip arms to actuate the plication clip to a closed position, to an open position, and to lock the plication clip in a closed position, wherein the plication clip has a outer diameter in a closed position ranging from 5 Fr to 22 Fr (1.66 mm to 7.33 mm) for catheter delivery; and (ii) a steerable catheter delivery apparatus, said apparatus comprising an external control unit connected to a flexible, elongated steerable catheter, said external control unit comprising an intra-lumen tool advance control, intra-lumen tool 3-axis control, intra-lumen tool rotational control, a distal anchor clamp control, and a distal tether tensioning control, wherein the dual-anchor dual tether device is configured to fit within a lumen of the steerable catheter delivery apparatus.

BRIEF DESCRIPTION OF THE SEVERAL VIEWS OF DRAWING

Figure 4:
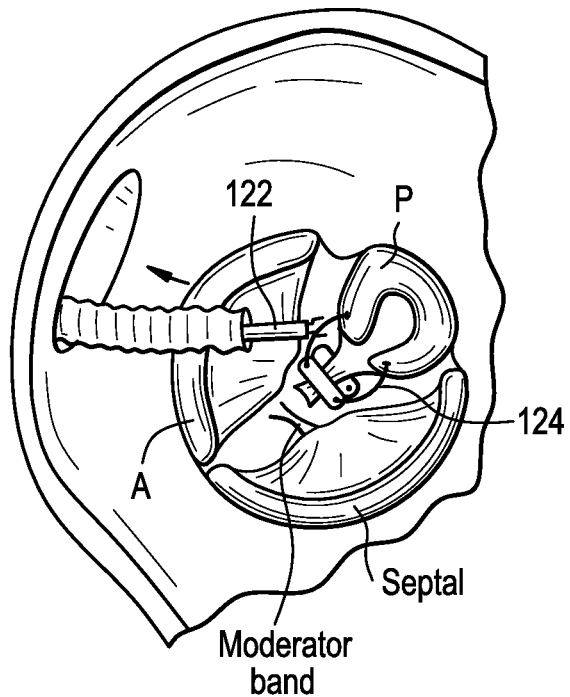

FIG. 4 is an illustration of a alternative technique for a plication clip delivered by steerable intracardiac catheter, attached to a target area of a posterior leaflet of a tricuspid valve, with a suturing tool for tethering the attached clip to one or more anchor points along the posterior annulus or the septomarginal trabecula, to secure the clip and complete the plicatation of the posterior annulus and leaflet to bicuspidize the triscuspid valve.

Figure 5:
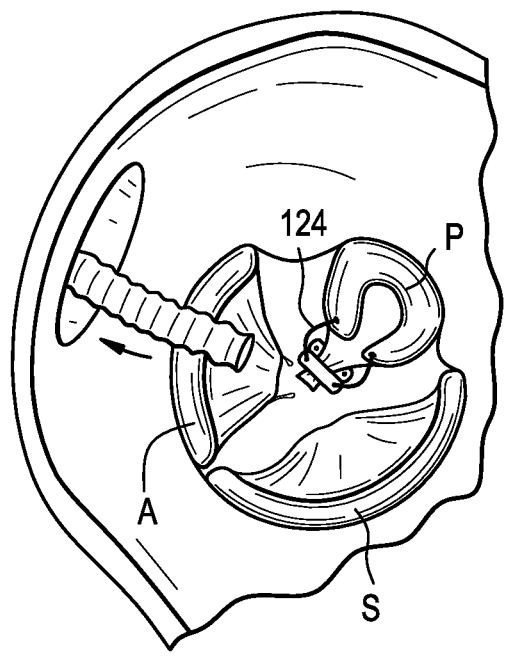

FIG. 5 is an illustration of a plication clip anchored or sutured to adjacent intra-ventricular or annular tissue that was delivered by steerable intracardiac catheter (shown being withdrawn), and attached to a target area of a posterior leaflet of a tricuspid valve, to secure the clip and complete the plicatation of the posterior annulus and leaflet to bicuspidize the triscuspid valve.

Figure 6:
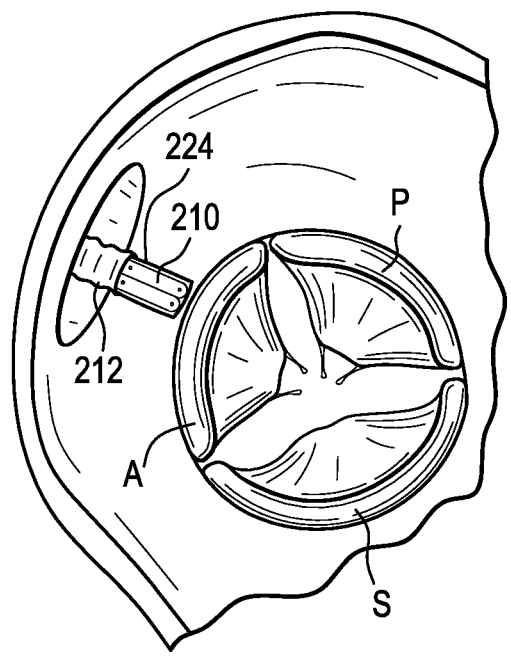

FIG. 6 is an illustration of another embodiment of a sheath-locked plication clip delivered by steerable intracardiac catheter and positioned to attach to a target area of a posterior leaflet of a tricuspid valve.

Figure 7:
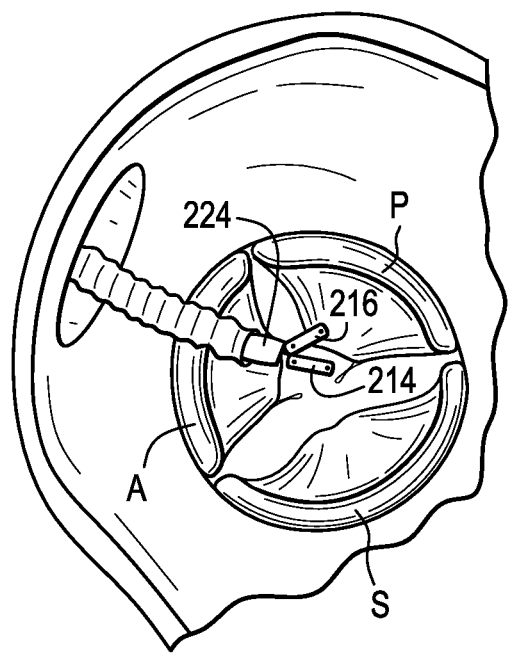

FIG. 7 is an illustration of a sheath-locked plication clip delivered by steerable intracardiac catheter and attached to a target area of a posterior leaflet of a tricuspid valve.

Figure 8:
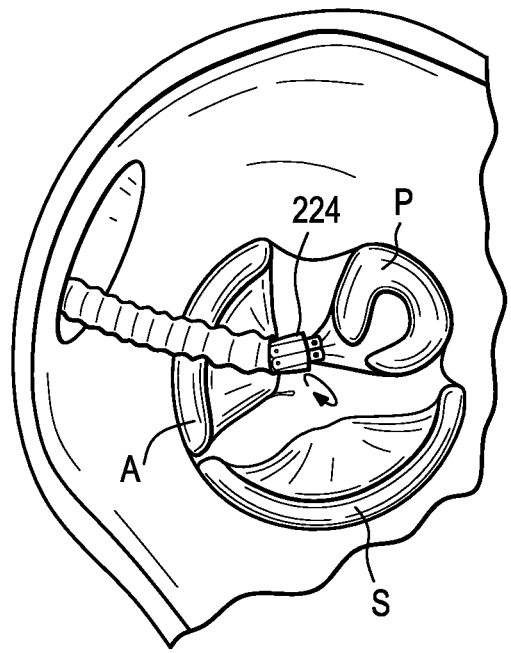

FIG. 8 is an illustration of a sheath-locked plication clip delivered by steerable intracardiac catheter, attached to a target area of a posterior leaflet of a tricuspid valve, with a positioning tool rotating the attached clip to cinch the leaflet and plicate the posterior annulus and leaflet to bicuspidize the triscuspid valve.

Figure 9:
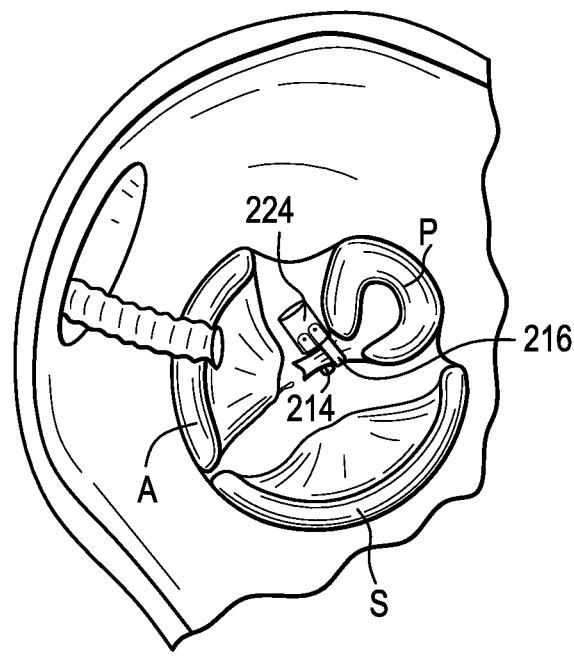

FIG. 9 is an illustration of a sheath-locked plication clip that was delivered by steerable intracardiac catheter (shown being withdrawn), and attached to a target area of a posterior leaflet of a tricuspid valve, to secure the clip and complete the plicatation of the posterior annulus and leaflet to bicuspidize the triscuspid valve.

Figure 10:
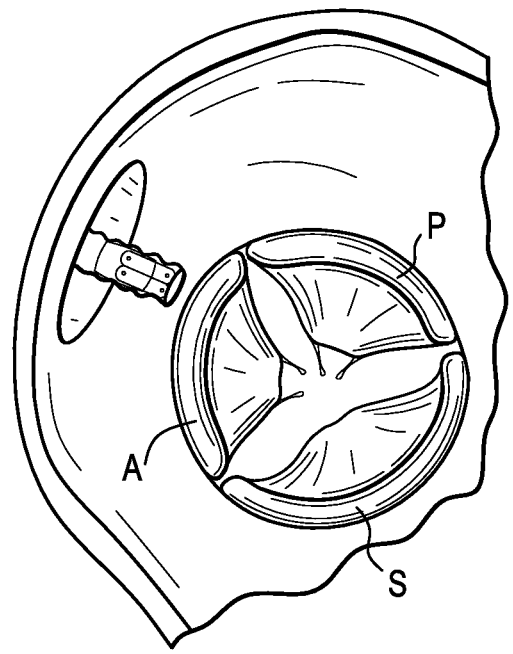

FIG. 10 is an illustration of delivery of another embodiment of a locking plication clip (either a sheath-locking or a double-clip locking) delivered by steerable intracardiac catheter and positioned to attach to a target area of a posterior leaflet of a tricuspid valve.

Figure 11:
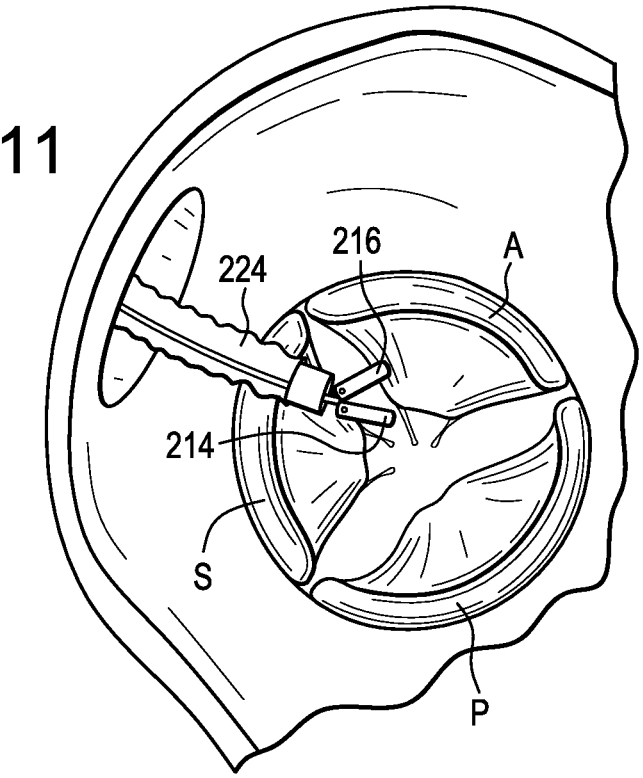

FIG. 11 is an illustration of a locking plication clip delivered by steerable intracardiac catheter and attached to a target area of a posterior leaflet of a tricuspid valve.

Figure 12:
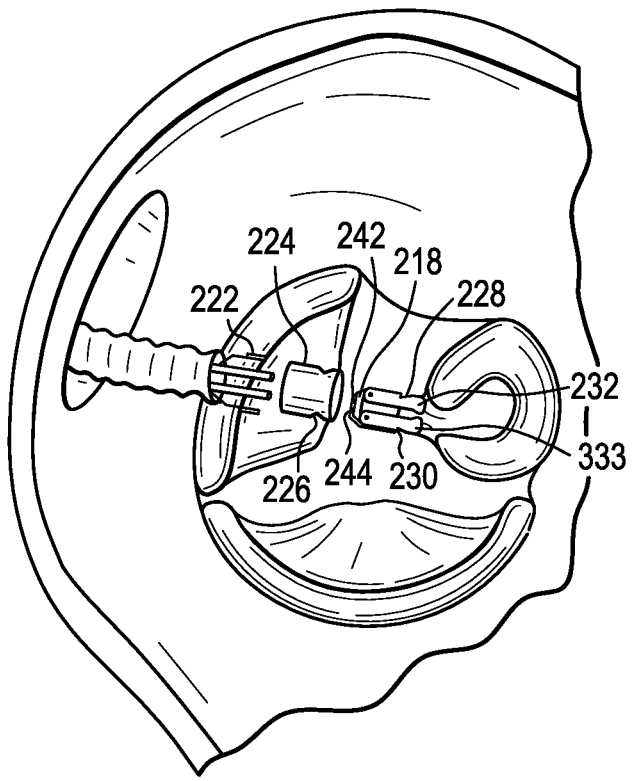

FIG. 12 is an illustration of another embodiment sheath-locked plication clip delivered by steerable intracardiac catheter, attached to a target area of a posterior leaflet of a tricuspid valve, with a positioning tool to cinch the leaflet, and a sheath tool to slide the sheath over the clip to plicate the posterior annulus and leaflet to bicuspidize the triscuspid valve.

Figure 13:
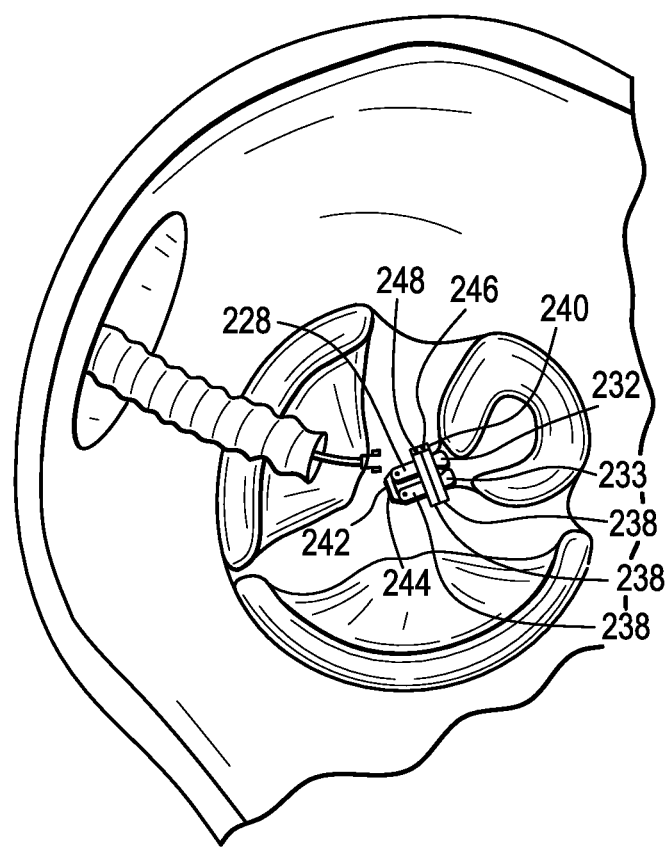

FIG. 13 is an illustration of a double clip-locked plication clip delivered by steerable intracardiac catheter, attached to a target area of a posterior leaflet of a tricuspid valve, with a positioning tool to cinch the leaflet, and a secondary fastener or clip to secure the clip attached to the leaflet tissue, thus plicating the posterior annulus and leaflet to bicuspidize the triscuspid valve.

Figure 14A:
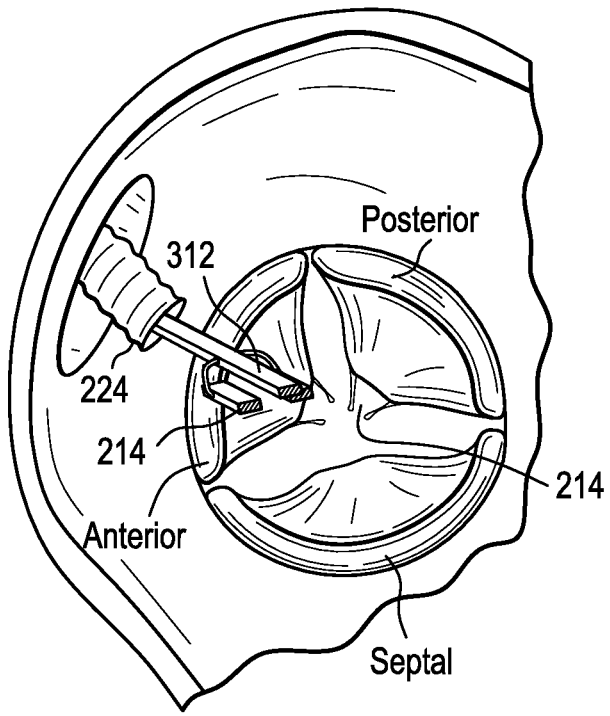
Figure 14B:
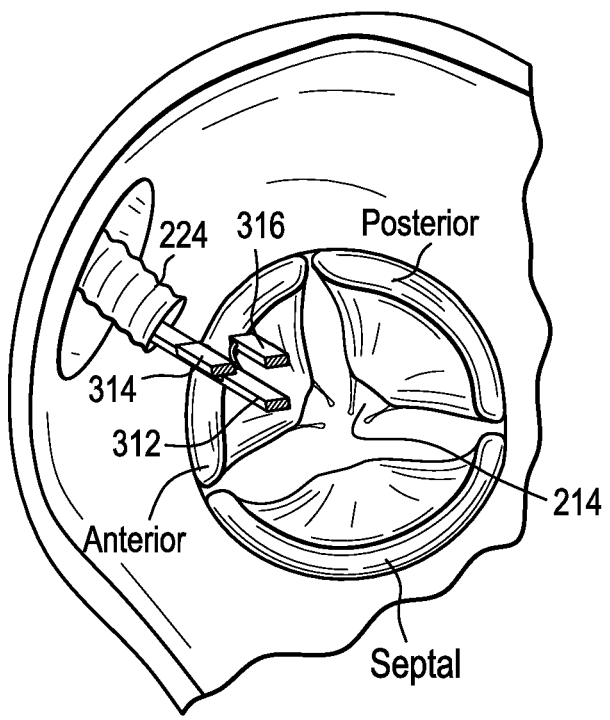

FIG. 14 is an illustration of a three-arm plication clip for a plication clip being delivered by steerable intracardiac catheter to a target area of a posterior leaflet of a tricuspid valve.

Figure 15:
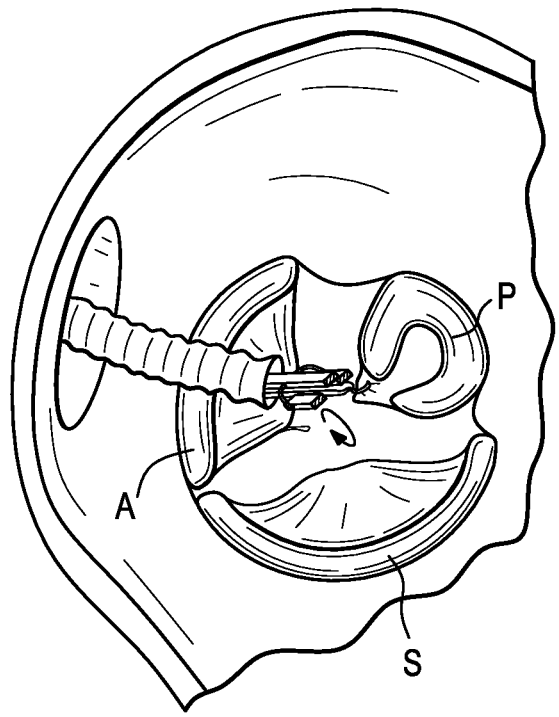

FIG. 15 is an illustration of another embodiment of three-arm plication clip having a centrally disposed tissue capture tool used to capture and align posterior leaflet or related tissue before the three-arm plication clip is actuated or scissor-clamped onto the target area of a posterior leaflet of a tricuspid valve.

Figure 16:
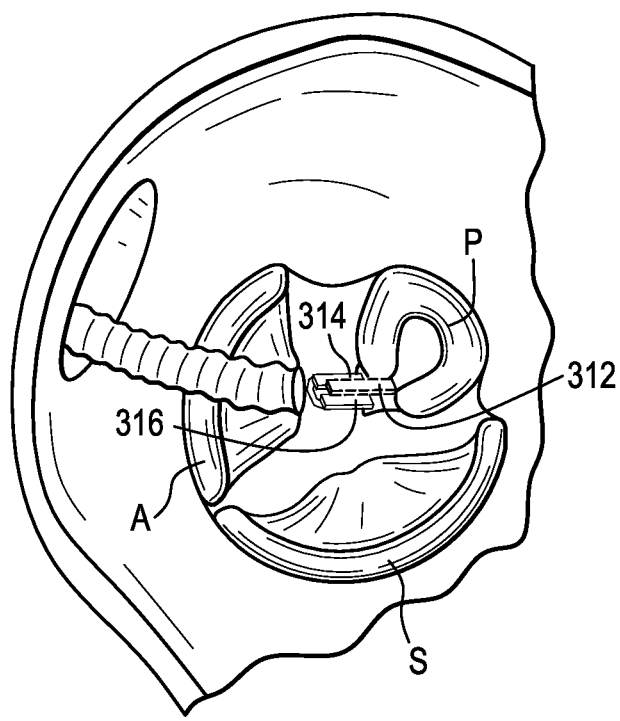

FIG. 16 is an illustration of a three-arm plication clip attached to posterior leaflet and nearby tissue, oriented after clamping with the central arm in the up position, and the two exterior arms in the down position.

Figure 17:
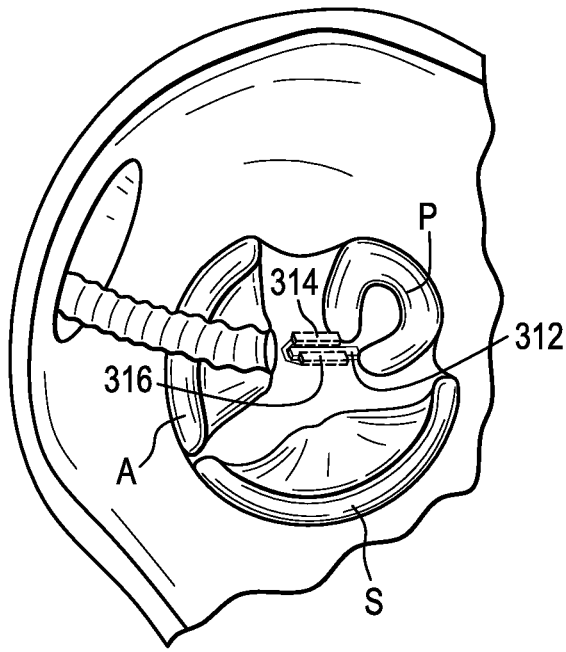

FIG. 17 is an illustration of a three-arm plication clip attached to posterior leaflet and nearby tissue, alternatively oriented after clamping with the central arm in the down position, and the two exterior arms in the up position.

Figure 18:
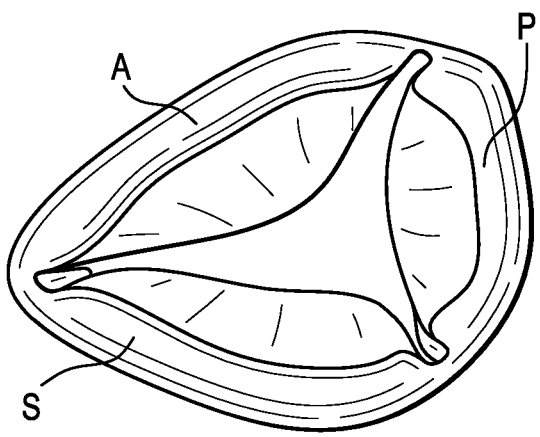

FIG. 18 is an illustration of a healthy tricuspid valve during systole when the contents of the right atrium are disgorged into the right ventricle.

Figure 19:
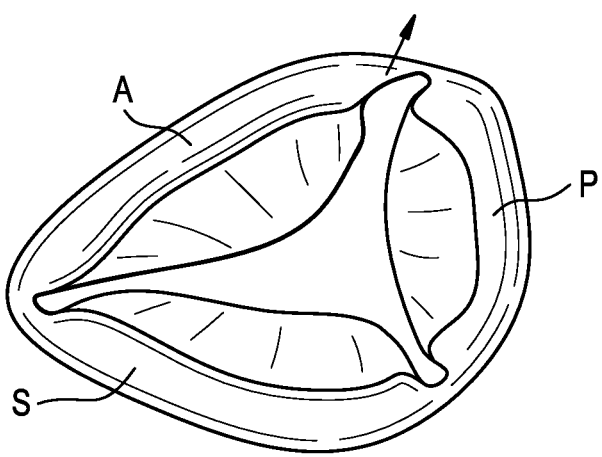

FIG. 19 is an illustration of a diseased, deformed, or damaged tricuspid valve during systole, and shows elongation along the anterior-posterior (A-P) line that is a cause of tricuspid valve regurgitation.

Figure 20:
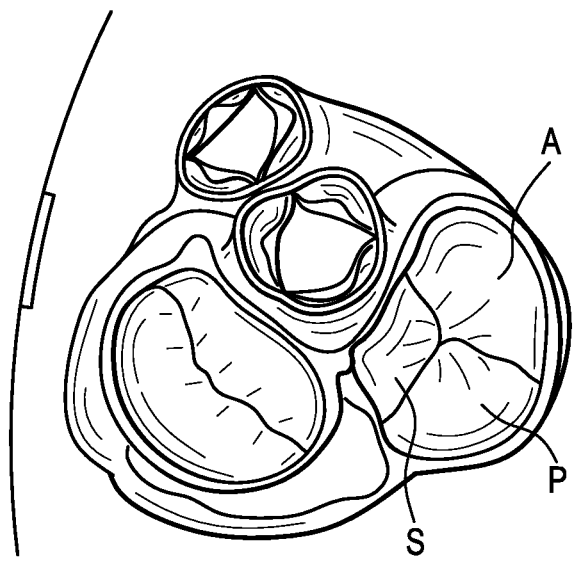

FIG. 20 is an illustration of a cross-sectional view of a heart showing the anatomy of the tricuspid valve and the geometry of the posterior, anterior, and septal valves during diastole.

Figure 21:
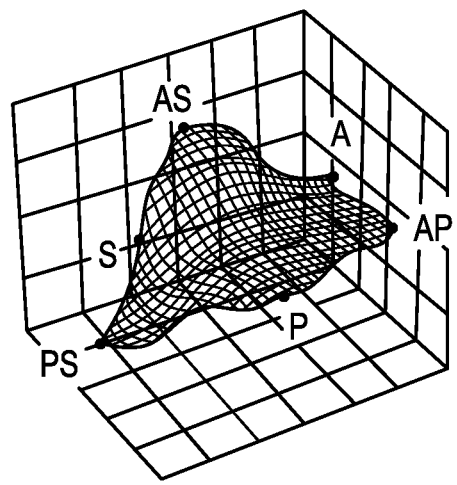

FIG. 21 is an illustration of the topological three-dimensional shape of the tricuspid valve.

Figure 22:
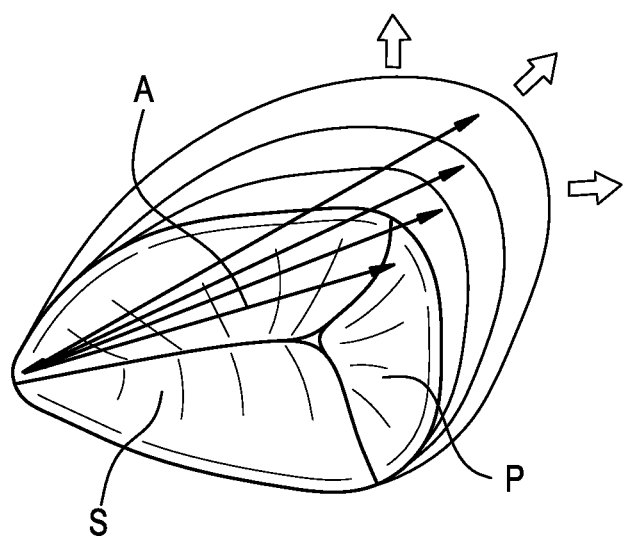

FIG. 22 is an illustration of a tricuspid valve during diastole and shows the direction of pathological deformation along the A-P axis perpendicular to the septal leaflet.

Figure 23:
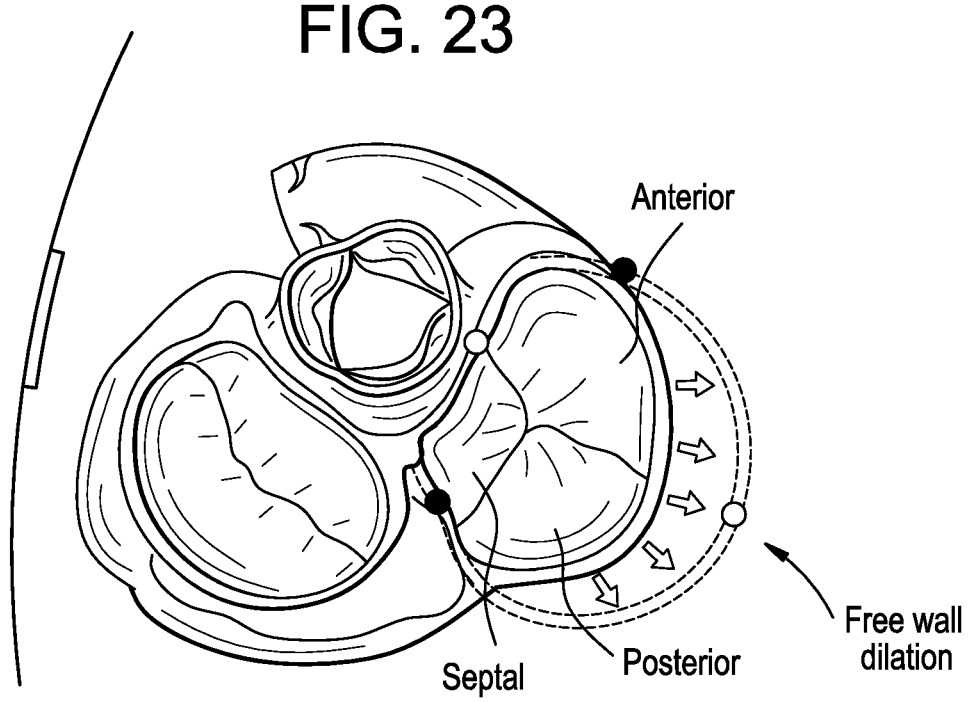

FIG. 23 is an illustration of a tricuspid valve during diastole and shows the direction of pathological deformation along the A-P axis with a view of the free wall dilatation that occurs with TVR.

Figure 24:
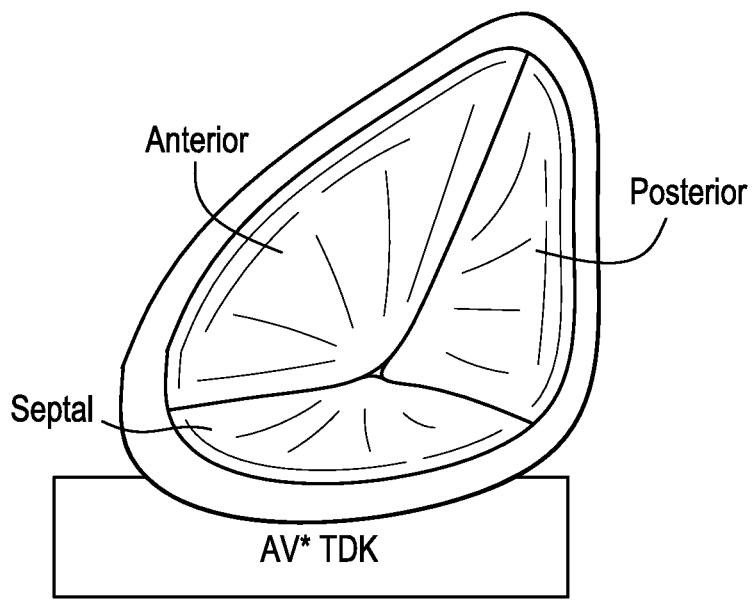

FIG. 24 is an illustration of a tricuspid valve during diastole and shows deformation along the A-P axis and identifies the location of AV node and the Triangle of Koch electrical bundle adjacent the septal annulus.

Figure 25:
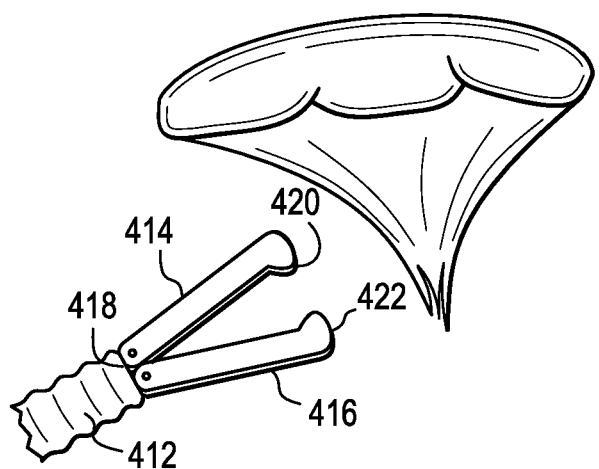

FIG. 25 is an illustration of another embodiment of a two-arm plication clip delivered by steerable intracardiac catheter and positioned to attach to a target area of a posterior leaflet of a tricuspid valve.

Figure 26:
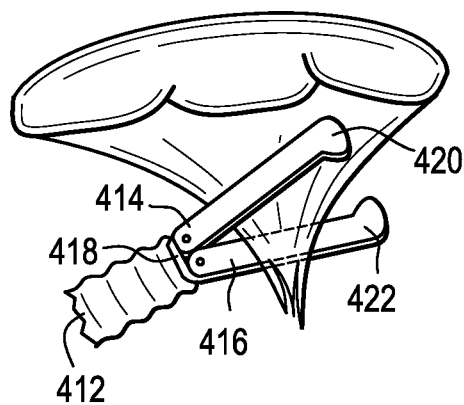

FIG. 26 is an illustration of a two-arm plication clip delivered by steerable intracardiac catheter and positioned to attach to a target area of a posterior leaflet of a tricuspid valve, and shows one arm positioned behind the posterior leaflet and chordae, and the second arm positioned in front of (nearest the central axis of the triscuspid aperture) the posterior leaflet and chordae.

Figure 27:
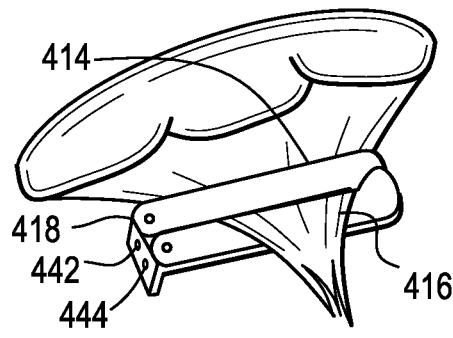

FIG. 27 is an illustration of a two-arm plication clip attached to a target area of a posterior leaflet of a tricuspid valve, and shows one arm positioned behind the posterior leaflet and chordae, and the second arm positioned in front of (nearest the central axis of the triscuspid aperture) the posterior leaflet and chordae, to cinch the leaflet and plicate the posterior annulus and leaflet to bicuspidize the triscuspid valve.

Figure 28:
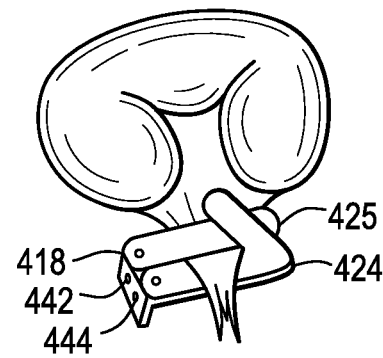

FIG. 28 is an illustration of a bend-locking two-arm plication clip attached to a posterior leaflet with one arm positioned in front and the second arm positioned behind the posterior leaflet and chordae and with the second arm bent to cinch and secure the posterior leaflet and chordae, to plicate the posterior annulus and leaflet and bicuspidize the triscuspid valve.

Figure 29:
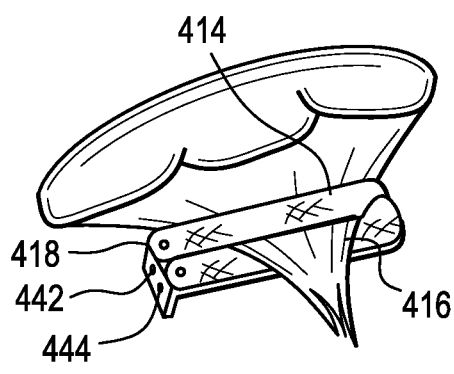

FIG. 29 is an illustration of a fabric covered two-arm plication clip attached to a target area of a posterior leaflet of a tricuspid valve, with one arm positioned behind the posterior leaflet and chordae, and the second arm positioned in front of the posterior leaflet and chordae, to cinch the leaflet and plicate the posterior annulus and leaflet to bicuspidize the triscuspid valve.

Figure 30:
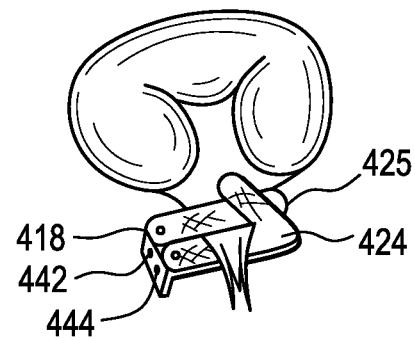

FIG. 30 is an illustration of a fabric covered bend-locking two-arm plication clip attached to a posterior leaflet with one arm positioned in front and the second arm positioned behind the posterior leaflet and chordae and with the second arm bent to cinch and secure the posterior leaflet and chordae, to plicate the posterior annulus and leaflet and bicuspidize the triscuspid valve.

Figure 31:
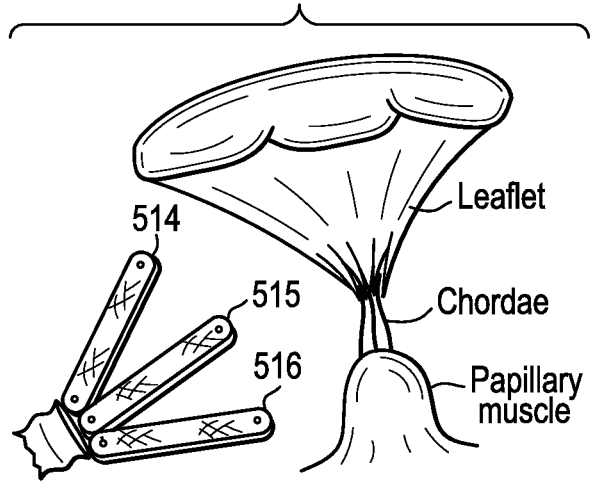

FIG. 31 is an illustration of a three-arm plication clip delivered by steerable intracardiac catheter and positioned to attach to a target area of a posterior leaflet of a tricuspid valve.

Figure 32:
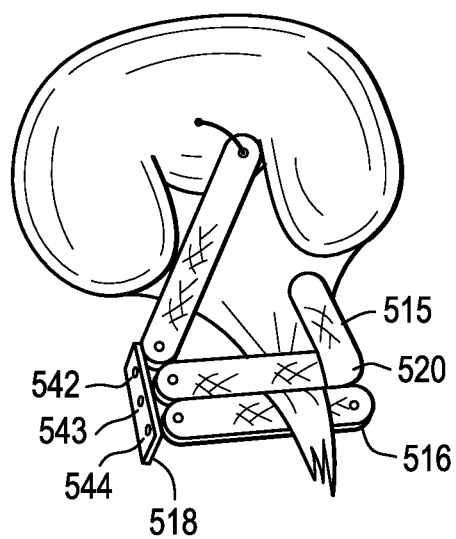

FIG. 32 is an illustration of a three-arm plication clip attached to a target area of a posterior leaflet of a tricuspid valve, and shows a first arm used to mechanically deform the posterior annulus into a plicated shape and sutured in place, a second arm positioned in front of the posterior leaflet and chordae, and the third arm positioned behind the posterior leaflet and chordae with the third arm bent to cinch and secure the posterior leaflet and chordae, resulting in a plicated leaflet and a functionally bicuspidized triscuspid valve.

Figure 33:
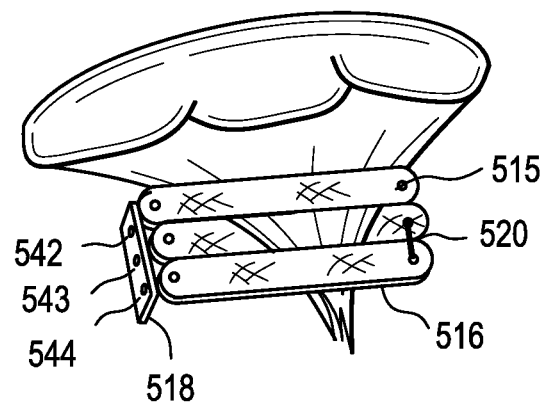

FIG. 33 is an illustration of a three-arm plication clip attached to a posterior leaflet with one (top) arm positioned in front, a second (middle) arm positioned behind the posterior leaflet and chordae, and a third (lower) arm positioned in from of the leaflet and chordae, and with fastening stitch or connector between the second and third arms to cinch and secure the posterior leaflet and chordae.

Figure 34:
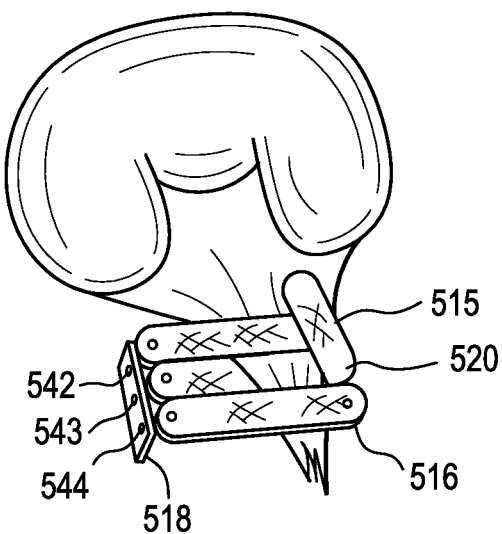

FIG. 34 is an illustration of a three-arm plication clip attached to a posterior leaflet with one (top) arm positioned in front, a second (middle) arm positioned behind the posterior leaflet and chordae that is bent to cinch and secure the posterior leaflet and chordae, and a third (lower) arm positioned in from of the leaflet and chordae.

Figure 35:
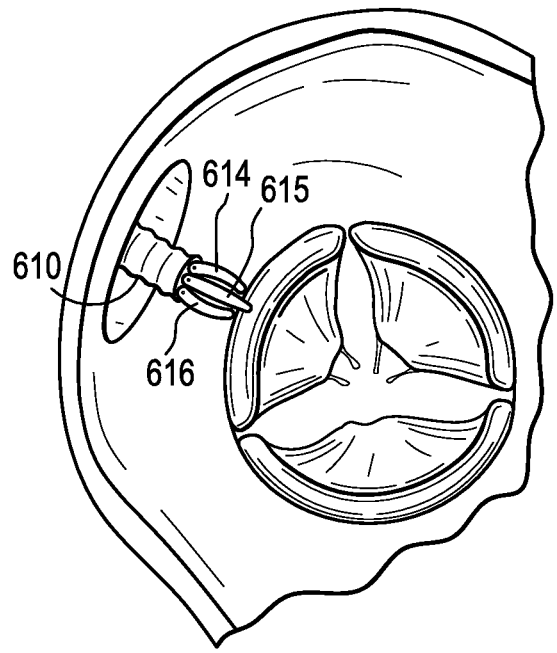

FIG. 35 is an illustration of a three-arm posterior annulus clip being delivered by catheter to the tricuspid valve.

Figure 36:
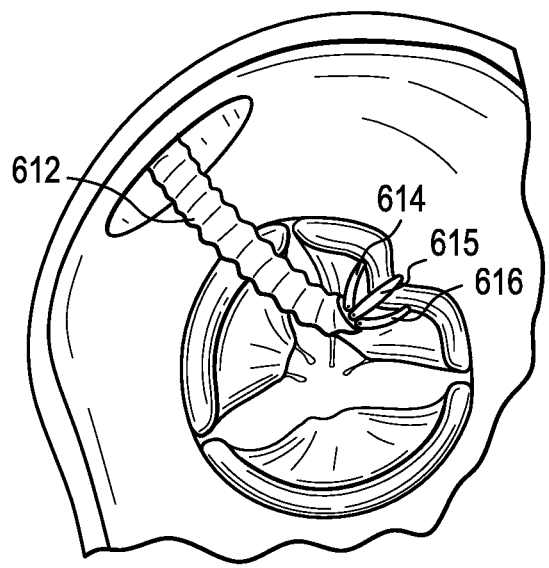

FIG. 36 is an illustration of a three-arm posterior annulus clip being attached to a target area of a posterior annulus of a tricuspid valve, and shows a first (middle) arm in between two parallel arms on each side of the middle arm, where the clip is used to mechanically deform the posterior annulus into a plicated shape by scissor-clamping/deforming the posterior annulus tissue.

Figure 37:
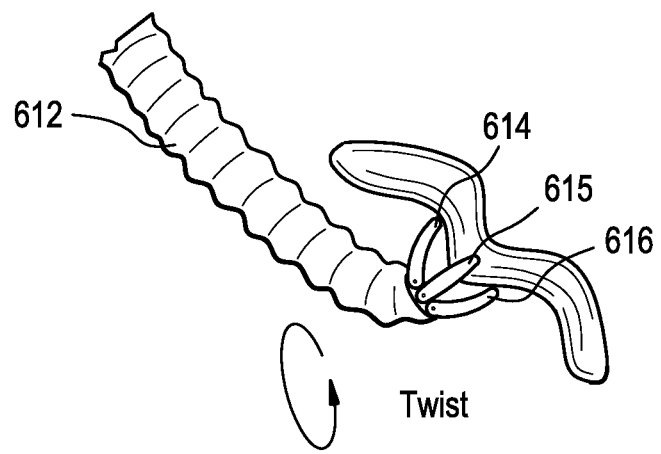

FIG. 37 is an illustration of an alternative embodiment of a three-arm posterior annulus clip having a twisting feature or step, for cinching and plicating the posterior annulus.

Figure 38:
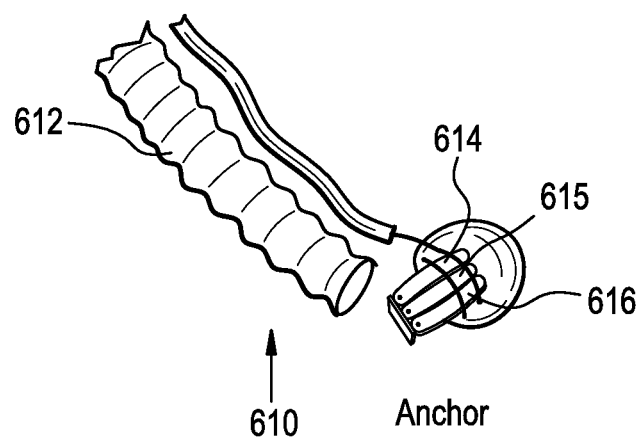
Figure 39:
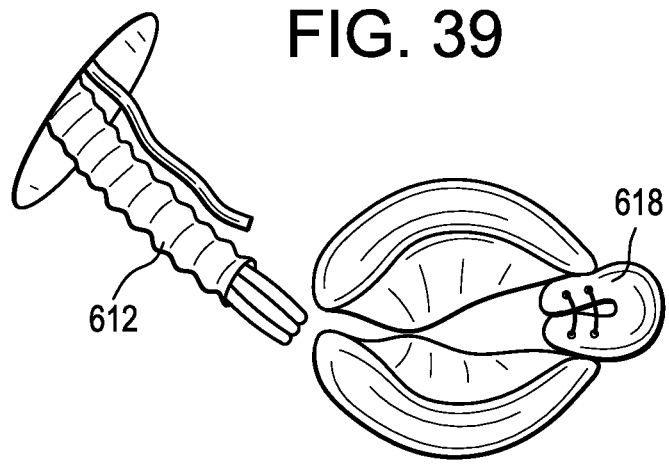

FIG. 38 is an illustration of another alternative embodiment of a three-arm posterior annulus clip having a suturing feature or step, for cinching and plicating the posterior annulus. The clip is detached from the delivery catheter and left in place in this embodiment FIG. 39 is an illustration of a triscuspid valve having a plicated posterior annulus functioning during diastole. In this embodiment of the three-arm posterior annulus clip, the clip is used solely for mechanically deforming the annulus and is removed after the annulus is sutured in a desired plicated shape.

Figure 40:
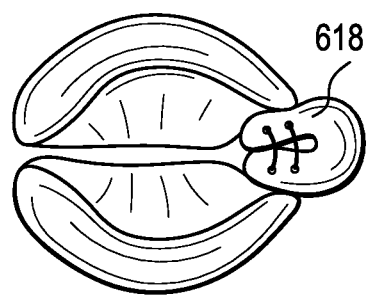

FIG. 40 is an illustration of a triscuspid valve having a plicated posterior annulus functioning during systole. In this embodiment, the clip is used solely for mechanically deforming the annulus and is removed after the annulus is sutured in a desired plicated shape.

down between, a second arm positioned in front of the posterior leaflet and chordae, and the third arm positioned behind the posterior leaflet and chordae with the third arm bent to cinch and secure the posterior leaflet and chordae, resulting in a plicated leaflet and a functionally bicuspidized triscuspid valve.

Figure 41:
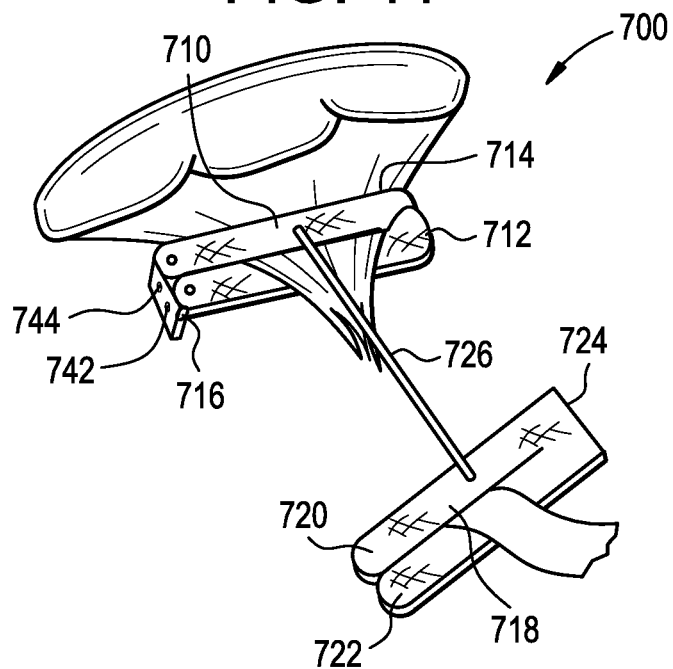

FIG. 41 is an illustration of a two-component tethered clip device deployed on a plicated tricuspid valve, where a (first) plication clip is used to plicate the posterior leaflet or annulus to the desired shape, and the first plication clip is tethered into position using a wire/rod/suture tether to a (second) moderator band clip that is mounted on the moderator band (septomarginal trabecula) within the right ventricle.

Figure 42:
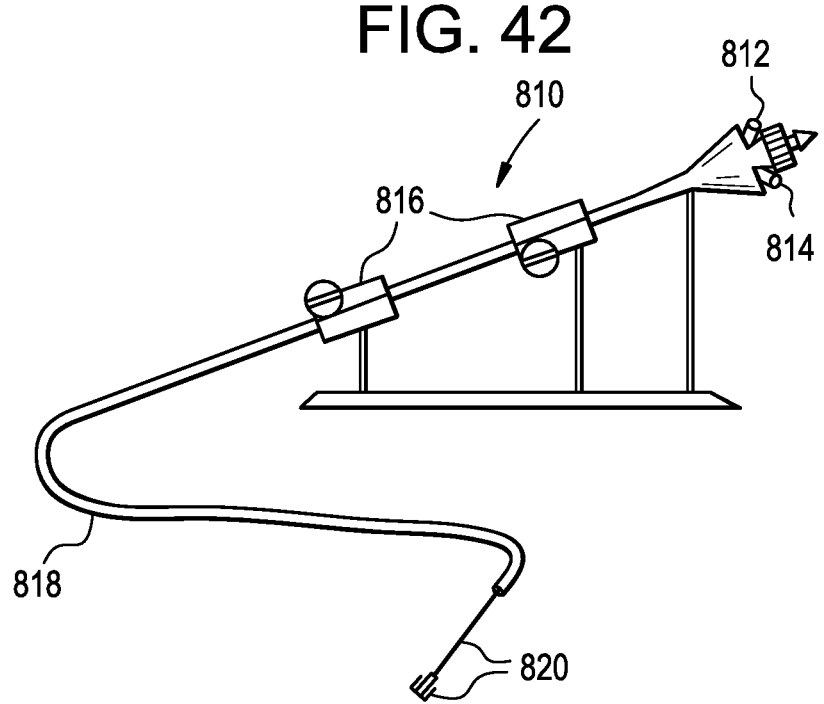

FIG. 42 is an illustration of one embodiment of a delivery system for use by an cardiac interventionist to deliver and deploy the clip devices to the posterior leaflet of the tricuspid valve for plicating the posterior leaflet and/or annulus to bicuspidize the triscuspid valve.

DETAILED DESCRIPTION OF THE INVENTION

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the Applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein the term "posterior leaflet complex" refers to the group of tissues including the posterior leaflet, the posterior annulus, and the chordae tendinae that attach the posterior leaflet to the posterior papillary muscle.

As used herein, the term "lumen" means a canal, a duct, or a generally tubular space or cavity in the body of a subject, including a catheter, a hollow needle, a tube, a vein, an artery, a blood vessel, a capillary, an intestine, and the like.

As used herein, the term "proximal" shall mean close to the operator (less into the body) and "distal" shall mean away from the operator (further into the body). In positioning a medical device inside a patient, "distal" refers to the direction away from a delivery catheter and "proximal" refers to the direction close to the delivery catheter.

As used herein, the term "wire" can be a strand, a cord, a fiber, a yarn, a filament, a cable, a thread, or the like, and these terms may be used interchangeably.

As used herein, the term "sheath" means cylindrical component that slides over a tissue clip, anchor, or fastening device having a slightly smaller diameter in cross-section. Where a tissue clip, anchor or fastener is made of spring material or is spring-actuated, a sheath may be used to lock the arms or jaws of the clip, anchor, or fastener into a closed position. It is contemplated that the sheath is made of Nitinol or similar material.

As used herein, the term "connector element" refers to any housing, hub, structure, frame, or support for attaching a proximal end of a clip arm. The "connector element" also includes one or more access ports for a catheter deployed positioning tool. The positioning tool may incorporate wire(s) that engage with a clip arm through the access port. It is contemplated that the connector element is made of Nitinol or similar material.

The term "clip arm" refers to one portion of a clamping structure for capturing tissue of the posterior leaflet complex of tissues. The use of a clip/clamp having multiple, two or more, clip arms is contemplated as within the scope of the invention. A clip arm may incorporate internally mounted wires for steerably moving each clip into varying shapes from elongate to curved to bent or to hooked. The wires are contemplated as running axially within each clip arm, but may also include longitudinal wire(s), helical wire(s), traversing wire(s), and circumferential wire(s). The positioning tool may also use the internal wires to lock each clip arm into a closed position relative to the other clip arms. It is also contemplated that the clip arms may have one or more suturing holes or suture anchoring structures on their surface. It is contemplated that the plication clip arms are made of Nitinol or similar material.

The term "closed position" refers to a configuration that has captured tissue of the posterior leaflet complex. Closed position may include two parallel elongate arms side-by-side, two elongate arms with at least one of them steered into a hook configuration, and so forth.

The term "open position" refers to a configuration that is open and permits the capture of tissue of the posterior leaflet complex. Examples include an open jaw of two straight arm, an open jaw of steerably curved arms, and so forth.

The term "check knob" refers to a structure at the distal end of a clip arm that projects towards an adjacent or opposing clip arm to prevent captured tissue from slipping out of the plication clip during capture and closing of the clip arms. It is contemplated that each clip arm may have a check knob, and it is also contemplated that the check knobs may include a locking structure so that adjacent check knobs may be engaged to lock the clip arms in a closed position.

The term "French" refers to a catheter sizing convention of the internal diameter of a catheter, whereby each number French divided by 3 is equivalent to 1.0 millimeter (mm). For example, 22 Fr is 7.33 mm ID, and 6 Fr is 2.0 mm ID. Devices delivered by catheter are required to have a diameter no larger that the ID of the delivery catheter.

The following description refers to the FIGURES herein. A person with ordinary skill in the art would recognize that the figures and description thereto refer to various embodiments of the present teachings and, unless indicated otherwise by their contexts, do not limit the scope of the attached claims to the figures and/or description thereto.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least and not as an attempt to limit the application of the doctrine of equivalents to the scope of the attached claims, numerical parameters should be read in light of the number of reported significant digits and the application of ordinary rounding techniques.

The present teachings relate to devices and methods for treating a tricuspid regurgitation.

Over Wire Delivery

An aspect of the present teachings provides various embodiments of locating a first location on a posterior leaflet or cusp to plicate the posterior leaflet and thereby functionally bicuspidize the tricuspid valve.

A further aspect of the present teachings provides various embodiments of deploying a wire following by a conical spacer to permit a steerable catheter to access the tricuspid annulus.

A further aspect of the present teachings provides various embodiments of reducing the circumference of the tricuspid annulus. An exemplary method of the present teachings begins by percutaneously accessing the tricuspid annulus from a suitable venous access site. According to some embodiments, the venous access site is located near the jugular vein, superiorly, from the femoral vein, inferiorly, or from other suitable sites. According to some embodiments of the present teachings, a suitable guide is directed into the internal jugular vein, extends through the right brachiocephalic vein, the superior vena cava, and reaches the right atrium. The distal end of the guide remains inside the right atrium. The proximal end of the guide remains outside of the body. According to some embodiments, the guide could have a general straight profile. In another embodiment, the guide could have a curved distal portion. In some embodiments, the distal portion of the guide could have a pre-set fixed curved. In another embodiment, the distal portion of the guide could be deflectably curved by sections controlled by a clinician from outside of the body. The guide has an axial lumen extending from its proximal end through its entire length to its distal end. This axial lumen of the guide serves as a conduit, allowing one or more catheters to be slidably disposed within and providing access to the right heart chambers. According to some embodiments, the guide remains in place during the entire procedure. According to some embodiments, the guide is removed, for example, during the procedure when other suitable means, such as a wire, maintains such a percutaneous access. According to some embodiments, the guide is a 12-24 French (F) catheter. According to some embodiments, the guide is a single lumen sheath (as catheter) that can accommodate all subsequent catheters to slide therein. Alternatively, in some embodiments, the guide is a multi-lumen sheath. It will be appreciated by persons of ordinary skill in the art that the size and the exact configuration of the guide is not limited to what is disclosed herein.

In various embodiments, a percutaneous repair of the tricuspid valve starts with identifying and obtaining an access to a location on the posterior cusp as well as a location on the tricuspid posterior annulus.

The invention includes an embodiment where a wire delivery catheter is directed into the right ventricle. In one embodiment, a wire delivery catheter is inserted from the proximal end of the guide through the lumen of the guide and reaches the right atrium. It is not necessary to enter the right ventricle for this procedure. One skilled in the art would understand that such an actuation can be accomplished by many mechanisms known in the field. According to some embodiments, the wire delivery catheter can be extended distally, retracted proximally, or turned axially.

According to some embodiments, a first leaflet and/or annulus location is identified by injecting a contrast dye inside the right coronary artery and the distal posterior descending artery. Alternatively, a location can be identified by advancing a radiopaque wire through the right coronary artery to the posterior descending artery. In various embodiments, the contrast dye and/or the radiopaque wire renders the right coronary artery visible under radiographic imaging equipment such as X-ray, magnetic resonance, ultrasound, fluoroscope, or other imaging techniques. By visualizing the right coronary artery and the posterior descending artery, a leaflet and/or annulus location can be identified. Upon identifying the leaflet and/or annulus location, in various embodiments, a clinician steers the wire delivery catheter so that, the distal end of the wire delivery catheter aligns at the tricuspid annulus, extends toward the right atrium, and contacts the tricuspid posterior leaflet and/or annulus at the location. According to one embodiment, the leaflet location (32) is directly between, at the midpoint between the commissures of the leaflet being anchored. A similar procedure is used to find a first annular location, and mount the annular anchor to the annulus at the first annular location.

Where a dual-tether dual-anchor device is used, a similar targeting process is used for the second location.

According to some embodiments, the steerable catheter is fitted with (tool is axially advance down lumen to the tissue worksite) a piercing tip which allows it to perforate the annulus. According to other embodiments, the steerable catheter is fitted with a radio frequency (RF) energy delivery tip to assist its location and crossing of the tricuspid annulus.

Figure 1:
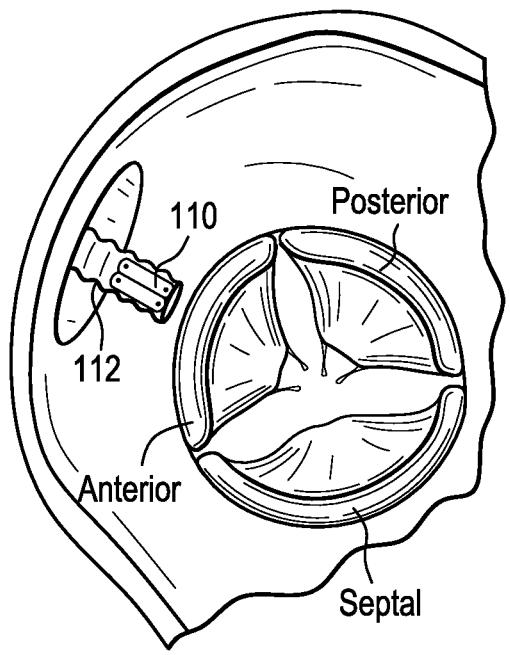
FIG. 1 is an illustration of one embodiment of a plication clip delivered by steerable intracardiac catheter and positioned to attach to a target area of a posterior leaflet of a tricuspid valve.
Figure 2:
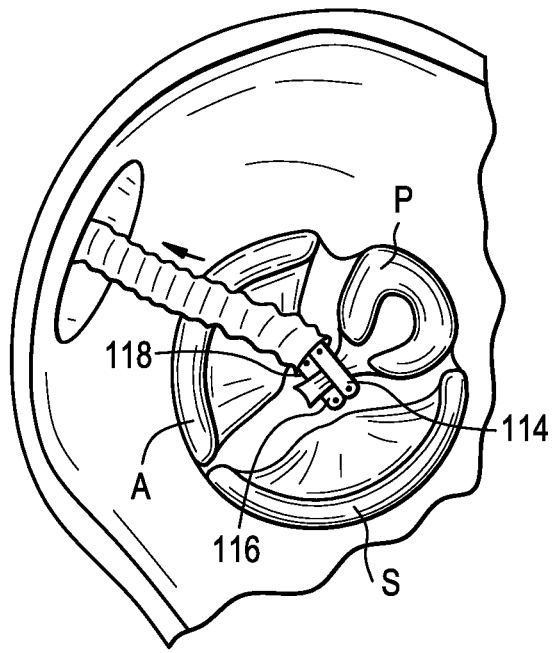
FIG. 2 is an illustration of one embodiment of a plication clip delivered by steerable intracardiac catheter and attached to a target area of a posterior leaflet of a tricuspid valve.
Figure 3:
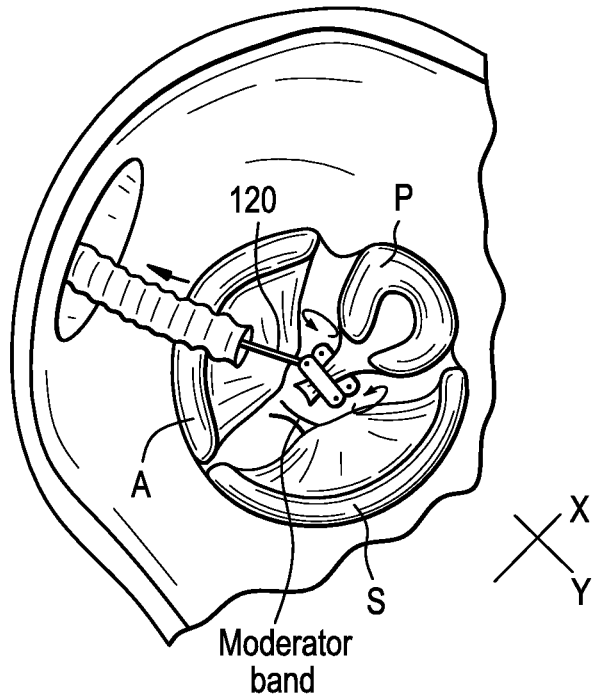
FIG. 3 is an illustration of a plication clip delivered by steerable intracardiac catheter, attached to a target area of a posterior leaflet of a tricuspid valve, with a positioning tool rotating the attached clip to cinch the leaflet and plicate the posterior annulus and leaflet to bicuspidize the triscuspid valve.

Referring now to FIG. 1 is an illustration of one embodiment of a plication clip 110 delivered by steerable intracardiac catheter 112 and positioned to attach to a target area of a posterior leaflet complex of a tricuspid valve. FIG. 1 shows the first elongate arm 114 and the second elongate arm 116 of the two-arm clip 110. FIG. 2 is an illustration of one embodiment of a plication clip 110 delivered by steerable intracardiac catheter 112 and attached to a target area of a posterior leaflet complex of a tricuspid valve. FIG. 2 shows the first arm 114 and the second arm 116 of the two-arm clip 110 delivered to the posterior leaflet complex where the arms 114, 116 have been actuated to open and receive the posterior leaflet complex tissue. First arm 114 is shown "in front" towards the center axis of the tricuspid aperture, and second arm 116 is shown positioned "behind" the posterior leaflet complex. FIG. 3 is an illustration of a plication clip 110 delivered by steerable intracardiac catheter 112, attached to a target area of a posterior leaflet complex of a tricuspid valve, with a positioning tool 120 rotating the attached clip 110 to cinch the leaflet and plicate the posterior annulus and leaflet to bicuspidize the triscuspid valve. FIG. 4 is an illustration of a alternative technique for a plication clip 110 delivered by steerable intracardiac catheter 112, attached to a target area of a posterior leaflet complex of a tricuspid valve, with a suturing tool 122 for tethering the attached clip 110 with a suture material 124 to one or more anchor points along the posterior annulus or the septomarginal trabecula, to secure the clip 110 and complete the plicatation of the posterior annulus and leaflet to bicuspidize the triscuspid valve. FIG. 5 is an illustration of a plication clip 110 anchored or sutured to adjacent intra-ventricular or annular tissue that was delivered by steerable intracardiac catheter 112 (shown being withdrawn), and attached to a target area of a posterior leaflet complex of a tricuspid valve, to secure the clip 110 and complete the plicatation of the posterior annulus and leaflet to bicuspidize the triscuspid valve.

FIG. 6 is an illustration of another embodiment of a sheath-locked plication clip 210 delivered by steerable intracardiac catheter 212 and positioned to attach to a target area of a posterior leaflet complex of a tricuspid valve. FIG. 7 is an illustration of a sheath-locked plication clip 210 delivered by steerable intracardiac catheter 212 and attached to a target area of a posterior leaflet complex of a tricuspid valve. FIG. 7 shows the first arm 214 and the second arm 216 of the two-arm clip 210 delivered to the posterior leaflet complex where the arms 214, 216 have been actuated to open and receive the posterior leaflet complex tissue. FIG. 7 shows sheath 224 being withdrawn to actuate the spring-loaded clip arms 214, 216. FIG. 8 is an illustration of a sheath-locked plication clip 210 delivered by steerable intracardiac catheter 212, attached to a target area of a posterior leaflet complex of a tricuspid valve, with a positioning tool 220 rotating the attached clip 210 to cinch the leaflet and plicate the posterior annulus and leaflet to bicuspidize the triscuspid valve. FIG. 8 shows sheath 224 being advanced to move the arms 214, 216 of clip 210 to a closed position. At this point, catheter 212 rotates the attached clip 210 to twist the captured leaflet tissue and cause plication of the posterior annulus and leaflet. A clinician can determine using imaging the amount of twisting necessary to achieve coaptation of the remaining, unmodified anterior and septal leaflets. FIG. 9 is an illustration of a sheath-locked plication clip 210 that was delivered by steerable intracardiac catheter 212 (shown being withdrawn), and attached to a target area of a posterior leaflet complex of a tricuspid valve, to secure the clip 210 and complete the plication of the posterior annulus and leaflet to bicuspidize the triscuspid valve. Advancing the sheath 224 locks the arms 214, 216 into a closed position to secure the plicated tissue, and then the catheter 212 is detached and withdrawn, leaving the clip 210 in place.

FIG. 10 is an illustration of delivery of another embodiment of a locking plication clip 210 (either a sheath-locking or a double-clip locking) delivered by steerable intracardiac catheter 212 and positioned to attach to a target area of a posterior leaflet complex of a tricuspid valve. FIG. 11 is an illustration of a sheath-locked plication clip 210 delivered by steerable intracardiac catheter 212 and attached to a target area of a posterior leaflet complex of a tricuspid valve. FIG. 11 shows the first arm 214 and the second arm 216 of the two-arm clip 210 delivered to the posterior leaflet complex where the arms 214, 216 have been wire actuated to open and receive the posterior leaflet complex tissue. FIG. 12 is an illustration of another embodiment sheath-locked plication clip 210 delivered by steerable intracardiac catheter 212, attached to a target area of a posterior leaflet complex of a tricuspid valve, with a positioning tool 220 to cinch the leaflet, and a sheath tool 221 to detach the slidable sheath 224, and slide the sheath 224 over the clip 210 to lock the arms 214, 216 into a closed position, thus plicating the posterior annulus and leaflet to bicuspidize the triscuspid valve. Inset of FIG. 12 shows clip 210 having first arm 214 and second arm 216 connected by a seating hub or frame 218. Arms 214, 216 each have a clip arm notch for engaging with a projection, or sheath lock 226, disposed on the interior surface of the cylindrical sheath 224. Arms 214, 216 also each have a distal projection, or check knob 232, 233, located at a distal end of each respective arm 214, 216 for grasping, capturing, and enclosing the leaflet tissue encompassed within the jaws of the arms 214, 216. Positioning tool 220, shown here as two actuating wires, engage with clip hub 218 at positioning tool access ports 242, 244. Sheath tool 222, shown here as two pushing wires with bumpers, engage with the proximal edge of sheath 224 to advance the sheath away from the catheter 212 and slide over the outer circumference of the clip 210 until the sheath lock 226 projection engages and locks into the notches 228, 230 of the clip arms 214, 216. FIG. 13 is an illustration of a double clip-locked plication clip 210 delivered by steerable intracardiac catheter 212, attached to a target area of a posterior leaflet complex of a tricuspid valve, with a positioning tool 220 to cinch the leaflet, and a secondary fastener or clip 234 to secure the cinching clip 210 attached to the leaflet tissue, thus plicating the posterior annulus and leaflet to bicuspidize the triscuspid valve. FIG. 13 shows arms 236, 238 of the second fastening clip 234 actuated by a positioning tool 220 engaging with tool access ports 246, 248 to open and perpendicularly fasten onto and secure cinching clip 210.

FIG. 14 is an illustration of a three-arm plication clip 310 for a plication clip being delivered by steerable intracardiac catheter to a target area of a posterior leaflet complex of a tricuspid valve. FIG. 14 shows three arm clip 310 having central, middle arm 312, first outer arm 314, and second outer arm 316. FIG. 14 inset shows how posterior leaflet complex tissue is targeted for capture as a relatively planar surface, wherein leaflet tissue upon capture would lay on top of outer arms 314, 316 and underneath middle scissoring arm 312. Upon actuating the three-arm clip 310 using the catheter, middle scissoring arm 312 moves between the outer arms 314, 316 to a position approximately equal to or below outer arms 314, 316, effecting a folding or pinching capture of the planar leaflet tissue. FIG. 15 is an illustration of another embodiment of three-arm plication clip 310 having a centrally disposed tissue capture tool 318 used to capture and align posterior leaflet complex or related tissue before the three-arm plication clip 310 is actuated or scissor-clamped onto the target area of a posterior leaflet complex of a tricuspid valve. FIG. 16 is an illustration of a three-arm plication clip 310 attached to posterior leaflet complex and nearby tissue, oriented after clamping with the central arm 312 in the up position, and the two exterior arms 314, 316 in the down position. FIG. 17 is an illustration of a three-arm plication clip 310 attached to posterior leaflet complex and nearby tissue, alternatively oriented after clamping with the central arm 312 in the down position, and the two exterior arms 314, 316 in the up position.

Tricuspid Issues

When considering how best to address problems with the tricuspid valve, e.g. regurgitation caused by disease, deformity, or injury, prior solutions fail to take into account that a regurgitant tricuspid has a specific shape and is attached between the right atrium and right ventricle having specific anatomical requirements. For example, FIG. 18 is an illustration of a healthy tricuspid valve during systole when the contents of the right atrium are disgorged into the right ventricle. However, FIG. 19 is an illustration of a diseased, deformed, or damaged tricuspid valve during systole, and shows elongation along the anterior-posterior (A-P) line that is a cause of tricuspid valve regurgitation. Annular rings and so forth that do not take into account the deformation along the A-P axis will not work in practice. Further, FIG. 20 is an illustration of a cross-sectional view of a heart showing the anatomy of the tricuspid valve and the geometry of the posterior, anterior, and septal valves during diastole. Note that the septal leaflet is smaller and is attached along a majority of its circumference to relatively immovable anatomical structure. FIG. 21 is an illustration of the topological three-dimensional shape of the tricuspid valve. Note that the tricuspid is a hyperbolic paraboloid in shape (like a stackable potato chip), but that the edge along the septal wall is nearly vertical, adding difficulties to attempting to repair a tricuspid by incorporating a septal leaflet intervention. Combine this with the complexity illustrated in FIG. 22 which shows a tricuspid valve during diastole and shows the direction of pathological deformation along the A-P axis perpendicular to the septal leaflet. Additionally, FIG. 23 shows a tricuspid valve during diastole and shows the direction of pathological deformation along the A-P axis with a view of the free wall dilatation that occurs with TVR. An additional concern with tricuspid intervention is shown in FIG. 24. FIG. 24 identifies the location of AV node and the Triangle of Koch electrical bundle adjacent the septal annulus, and raises the issue of complications arising from interfering with the cardiac electrical system, and specifically, the care that must be take to not damage the tissues responsible for the electrical conduction within the heart muscle.

Additional Embodiments

FIG. 25 is an illustration of another embodiment of a two-arm plication clip 410 delivered by steerable intracardiac catheter 412 and positioned to attach to a target area of a posterior leaflet complex of a tricuspid valve. FIG. 25 shows check knobs 420, 422 located at a distal end of each respective arm 414, 416 for grasping, capturing, and enclosing the leaflet tissue encompassed within the jaws of the arms 414, 416. FIG. 26 is an illustration of a two-arm plication clip 410 delivered by steerable intracardiac catheter 412 and positioned to attach to a target area of a posterior leaflet complex of a tricuspid valve. FIG. 26 shows the arms 414. 416 with one arm positioned behind the posterior leaflet complex and chordae, and the second arm positioned in front of (nearest the central axis of the triscuspid aperture) the posterior leaflet complex and chordae. FIG. 27 shows the clip 410 attached to the posterior leaflet complex of a tricuspid valve, with the leaflet tissue secured between the arms 414, 416 and prevented from detachment by check knobs 420, 422. FIG. 27 shows arms 414, 416 with one arm positioned behind the posterior leaflet complex and chordae, and the second arm positioned in front of (nearest the central axis of the triscuspid aperture) the posterior leaflet complex and chordae, to cinch the leaflet and plicate the posterior annulus and leaflet to bicuspidize the triscuspid valve. FIG. 27 shows clip hub 418 with positioning tool access ports 442, 444 that permit the positioning tool 420 (not shown) to actuate (open and close) the jaws/arms 414, 416 with two actuating wires.

In another variation or preferred embodiment of the invention, FIG. 28 illustrates a bend-locking two-arm plication clip 410 attached to a posterior leaflet complex with bendable arms 424, 425, with one arm positioned in front and the second arm positioned behind the posterior leaflet and chordae. In a first step of a bent-anchor fastening process, the arms 424, 425 are straight and are fastened onto the leaflet tissue similar to FIG. 27. In a second step of a bent-anchor fastening process, the arms 424, 425 are each bent to cinch and secure the posterior leaflet and chordae, to plicate the posterior annulus and leaflet and bicuspidize the triscuspid valve. FIG. 28 shows clip hub 418 with positioning tool access ports 442, 444 that permit the positioning tool 420 with the with two actuating wires (not shown) to actuate the jaws/arms 424, 425 in both Step 1 (open and close), and in Step 2 bending of each arm into a hook configuration, with the pair of arms assembled in their final configuration as interleaved hook anchors. FIG. 29 is an illustration of a fabric 426 covered two-arm plication clip 410 attached to a target area of a posterior leaflet complex of a tricuspid valve, with one arm positioned behind the posterior leaflet and chordae, and the second arm positioned in front of the posterior leaflet and chordae, to cinch the leaflet and plicate the posterior annulus and leaflet to bicuspidize the triscuspid valve. FIG. 30 is an illustration of a fabric 426 covered bend-locking two-arm plication clip attached to a posterior leaflet complex with one arm positioned in front and the second arm positioned behind the posterior leaflet and chordae, and with the arms bent to cinch and secure the posterior leaflet and chordae, to plicate the posterior annulus and leaflet and bicuspidize the triscuspid valve.

Referring now to FIG. 31, a three-arm plication clip 510 delivered by steerable intracardiac catheter 512 is illustrated and is shown as positioned to attach to a target area of a posterior leaflet complex of a tricuspid valve. FIG. 32 shows one configuration of the three-arm plication clip 510, and shows a first arm 514 used to mechanically deform the posterior annulus into a plicated shape and be sutured in place, a second arm 515 positioned in front of the posterior leaflet and chordae, and the third arm 516 positioned behind the posterior leaflet and chordae. The third arm is then bent 516 into a hook configuration to cinch and secure the posterior leaflet and chordae. Similar to FIG. 32, FIG. 34 shows a three-arm plication clip attached to a posterior leaflet complex with one (top) arm positioned in front, a second (middle) arm positioned behind the posterior leaflet and chordae that is bent to cinch and secure the posterior leaflet and chordae, and a third (lower) arm positioned in from of the leaflet and chordae. As illustrated herein, clip hub 518 has positioning tool access ports 542, 544 that permit a positioning tool with two actuating wires (not shown) to actuate the jaws/arms 514, 515, 516 in both Step 1 (open and close), and in Step 2 bending of an arm into a hook configuration, with the arms assembled in their final configuration as interleaved hook anchors.

FIG. 33 shows another configuration of the three-arm plication clip 510 having a fastening stitch 520, wherein it is attached to a posterior leaflet complex with one (top) arm 514 positioned in front, a second (middle) arm 515 positioned behind the posterior leaflet and chordae, and a third (lower) arm 516 positioned in from of the leaflet and chordae. The fastening stitch or connector 520 is attached to and spans between the second and third arms to cinch and secure the posterior leaflet and chordae.

FIG. 35 is an illustration of a three-arm posterior annulus clip 610 used for plicating the annulus, where the annular tissue is secured with suture or tissue anchors 618, and the annulus clip 610 is either detached to remain in place or is removed after the suture or anchor(s) are deployed. FIG. 36 shows the three-arm posterior annulus clip 610 deforming a target area of a posterior annulus of a tricuspid valve, and shows a first (middle) arm 614 in between two parallel arms 615, 616 on each side of the middle arm 614, where the clip 610 is used to mechanically deform the posterior annulus into a plicated shape by scissor-clamping/deforming the posterior annulus tissue. FIG. 37 illustrates a twisting feature or step, for cinching and plicating the posterior annulus. FIG. 38 shows the clip 610 is detached from the delivery catheter 612 and left in place in this embodiment. FIG. 39 shows an embodiment where annulus clip 610 is removed after the suture or anchor(s) are deployed, leaving only the sutures or anchors behind. FIG. 40 is an illustration of a triscuspid valve having a plicated posterior annulus functioning during systole as a functionally bicuspidized triscuspid valve.

FIG. 41 is an illustration of a two-component tethered clip device 700 deployed on a plicated tricuspid valve, where a proximal plication clip 710 is used to plicate the posterior leaflet complex (leaflet, annulus, chordae) to the desired shape, and the proximal plication clip 710 is tethered into position using a wire/rod/suture tether 726 to a (second) moderator band clip 718 that is mounted on the moderator band (septomarginal trabecula) within the right ventricle. Proximal clip 710 is deployed onto posterior leaflet complex, which is sandwiched between first arm 712 and second arm 714. Proximal clip hub 716 provides positioning tool access ports 742, 744. Distal clip 718 is deployed onto septomarginal trabecula, which is sandwiched between distal clip first arm 720 and distal clip second arm 722. Distal clip hub 724 provides positioning tool access ports 743, 745.

FIG. 42 is an illustration of one embodiment of a delivery system 810 for use by an cardiac interventionist to insert and deploy the clip devices to the posterior leaflet complex of the tricuspid valve for plicating the posterior leaflet and/or annulus to bicuspidize the triscuspid valve. FIG. 42 shows delivery system 810 having access port 812, axial control 814, and directional control 816. Delivery catheter 818 leads from the external control and tool exchange ports to the deployment site within the patient for delivery of various catheter tools 820, including pre-folded and packaged clip capsules 822, anchors, and so forth.

Tethers, Anchors

Preferably, the plication clip, tether and anchors are made from superelastic metal wire, such as Nitinol™ wire or other similarly functioning material. It is contemplated as within the scope of the invention to use other shape memory alloys such as Cu—Zn—Al—Ni alloys, Cu—Al—Ni alloys, as well as polymer composites including composites containing carbon nanotubes, carbon fibers, metal fibers, glass fibers, and polymer fibers. It is contemplated that the tether may be constructed as a braided or as a laser cut. Such devices are available from any number of commercial manufacturers, such as Pulse Systems. Laser cut devices are preferably made from Nickel-Titanium (Nitinol™), but also without limitation made from stainless steel, cobalt chromium, titanium, and other functionally equivalent metals and alloys, or Pulse Systems braided that is shape-set by heat treating on a fixture or mandrel.

Tethers may be made from surgical-grade materials such as biocompatible polymer suture material. Non-limiting examples of such material include ultra high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the stent body, pierce, rotate into, and hold annular tissue securely.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Tissue Clips, Anchors, Fasteners

As additional assistive devices used along with the plication clip here, it is contemplated that standard tissue clip, anchor, or fastening devices known in the art can be used along with the plication clip, provided they can be packaged and delivered via catheter, e.g. fit within the internal diameter (ID) of the delivery catheter (5 Fr-22 Fr). In various embodiments, a tissue anchor comprises a plurality of discrete, flat, or flexible anchor elements coupled with a flexible tensile member or tether. The anchor elements can be made from a surgical grade fabric material (e.g., a polyester material such as DACRON), in some instances, designed to promote tissue in-growth so that the anchors (310 a) become at least in part encased in tissue over-time. The anchor elements are coupled to a tensile member, in this example, a suture, by threading the suture distally through the anchor elements and proximally through the anchor elements. A slip knot or another type of locking mechanism is formed so that when a proximal end portion of the tensile member is pulled, all of the anchor elements will be drawn together. This leaves a long "tail" of the suture leading from the anchor to the venous access site and the long "tail" can be used for subsequent tensioning and plication, as described herein.

Examples of a tissue anchor and a tissue anchor delivery catheter described in conjunction with the drawings of the present teachings have some similarities to those in U.S. patent application Ser. No. 12/273,670, filed on Nov. 19, 2008, entitled Tissue Anchor and Anchoring System, U.S. patent application Ser. No. 11/174,951, filed on Jul. 5, 2005, entitled Tissue Anchor, Anchoring System and Methods of Using the Same, U.S. patent application Ser. No. 13/777, 042, filed on Feb. 26, 2013, entitled Tissue Anchor and Anchoring System, each of which is incorporated by reference herein in its entirety. Though not shown in the exemplary figures, other suitable tissue anchors can also be used. Examples of suitable tissue anchors include, but are not limited to, tissue fasteners, tissue pledgets, or tissue staples etc.

Multiple Clips, Anchors

Additionally, although three tissue anchors are illustrated herein, more than three tissue anchors can also be used without departing from the scope of the present teachings. According to some embodiments, tension is applied to all tissue anchors and secured by one locker. According to other embodiments, tension is applied to two of the tissue anchors at a time.

According to some embodiments, each tissue anchor is deployed sequentially. Specifically, the embodiments described allow a clinician to place a wire at the first leaflet location, followed by deploying a first leaflet anchor over the wire, and then manipulate the same wire delivery mechanism and place the wire at a next location, followed by deploying the next device over the wire. According other embodiments, two or more tissue clips or anchors are deployed simultaneously. Specifically, a multi-lumen translation catheter can be used to place two wires at two locations at the same time. According to other embodiments, a catheter with more than two branches can be used to place multiple wires at multiple locations at the same time.

The multi-lumen translation described in conjunction with the drawings of the present teachings have some similarities to those in U.S. patent application Ser. No. 11/685,239, filed on Mar. 13, 2007, entitled Systems and Methods for Introducing Elements Into Tissue; U.S. patent application Ser. No. 11/685,240, filed on Mar. 13, 2007, entitled Tissue Anchors, Systems, and Methods, and Devices; U.S. patent application Ser. No. 11/685,242, filed on Mar. 13, 2007, entitled Devices and Methods For Introducing Elements into Tissue; and U.S. patent application Ser. No. 13/282,139, filed on Oct. 26, 2011, entitled Hand Operated Device for Controlled Deployment of a Tissue Anchor and Method of Using the Same; each of which is incorporated in its entirety by reference herein.

Connected Anchors

In alternative embodiments of the present teaching, tricuspid annulus can be plicated by a chain of tissue anchors. In some embodiments, two or more tissue anchors are connected together by a tether or tensile member. In one embodiment, plication happens by pulling said tether or tensile member and thereby drawing all tissue anchors together.

To create a chain of plications, a clinician can then repeat method of tissue plication described above and extend the first tether or tensile member from the first tissue anchor to a second clip or anchor, and so forth. Plicating annulus tissue between the first tissue anchor and subsequent tissue anchors further reduces the size of the tricuspid valve orifice.

Plication distances can be adjusted such that a clinician can observe whether or the posterior, anterior and septal leaflets coapt as desired. A suture cutter can then be advanced to cut the tether or tensile members.

Imaging

According to various embodiments of the present teachings, a radioopaque marker or textured surface can be used to make the device visible by using radiographic imaging equipment such as an X-ray, magnetic resonance, ultrasound or other imaging technique. A marker disclosed herein may be applied to any part of the guide, catheter, or devices disclosed in present teachings. A radioopaque marker can be sewed, adhered, swaged riveted, or otherwise placed and secured on the guide, catheter, and/or devices, The radioopaque marker may be made from a material selected from tantalum, tungsten, platinum, iridium, gold, an alloy thereof, or another material known to those with ordinary skill in the art. The radioopaque marker can also be made from cobalt, fluorine, or another paramagnetic material, or another MR visible material known to those with ordinary skill in the arts. Additionally, a contrast media injected into the atrium, ventricle, or artery may also be used to confirm the positioning under a fluoroscope.

Terminology Guide

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the specification, including definitions, controls. In addition, the materials, methods, and examples are illustrative only and not intended to be limiting.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Functionally Equivalent Modifications

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having thus described the invention with the details and particularity required by the patent laws, what is claimed and desired protected by Letters Patent is set forth in the appended claims.

PARTS LIST

FIG. 1-5
110 two arm clip
112 delivery catheter
114 first arm of clip
116 second arm of clip
118 clip arm connector element
120 positioning tool
122 suture tool
124 suture
FIG. 6-13
210 two arm (cinching) clip
212 delivery catheter
214 first arm of clip
216 second arm of clip
218 clip arm connector element
220 positioning tool
222 sheath tool
224 sheath
226 sheath lock
228 clip arm notch 1
230 clip arm notch 2
232 clip arm check knob 1
233 clip arm check knob 2
234 2d fastening clip
236 2d clip first arm
238 2d clip second arm
240 2d clip connector element
242 positioning tool access port 1
244 positioning tool access port 2
246 2d clip positioning tool access port 1
248 2d clip positioning tool access port 2
FIG. 14—
310 three-arm clip
312 central/middle arm
314 outer arm 1
316 outer arm 2
318 tissue capture hook
FIGS. 25—
410 two arm clip
412 delivery catheter
414 first arm
416 second arm
418 clip connector element
420 clip arm check knob 1
422 clip arm check knob 2
424 bending arm 1
425 bending arm 2
426 fabric cover
442 positioning tool access port 1
444 positioning tool access port 2
FIGS. 31—
510 three arm clip
512 delivery catheter
514 first arm
515 second arm
516 third arm
518 clip connector element
520 fastener suture
524 bent portion
526 fabric cover
542 positioning tool access port 1
544 positioning tool access port 2
FIGS. 35—
610 three arm clip
612 delivery catheter
614 first arm
615 second arm
616 third arm
618 suture
FIG. 41
700 two-component tethered clip device
710 proximal two arm clip
712 first arm
714 second arm
716 clip connector element 1
742 positioning tool access port 1
744 positioning tool access port 2
718 distal two arm clip
720 first arm
722 second arm
724 clip connector element 2
743 positioning tool access port 1
745 positioning tool access port 2
726 moderator band tether
FIG. 42
810 delivery system
812 access port
814 axial control
816 directional control 818 delivery catheter
820 catheter tool
822 clip capsule

What is claimed is:

1. A method for percutaneously plicating a tricuspid posterior annulus within a heart of a patient comprising the steps of:
   (i) advancing a plication clip using a steerable delivery catheter deployed to a right atrium of the heart of the patient to a tissue location on the triscuspid posterior annulus;
   (ii) deploying the plication clip onto the tricuspid posterior annulus by actuating the plication clip from an open position to a closed position, where the plication clip comprises a connector element and a first elongate clip arm attached at a proximal end to the connector element and a second elongate clip arm attached at a proximal end to the connector element at a proximal end;
   wherein the open position of the deployed plication clip positions the tricuspid posterior annulus between the first elongate clip arm and the second elongate clip arm, and wherein the closed position of the deployed plication clip captures the tricuspid posterior annulus securely between the first and second elongate clip arms;
   (iii) actuating the closed plication clip to mechanically deform the tricuspid posterior annulus into a plicated shape to reduce annular diameter of and bicuspidize the tricuspid valve, wherein actuating the closed plication clip reduces annular distance between a postero-septal commissure and an antero-posterior commissure of the tricuspid valve; and
   (iv) securing in place the a fastener on the deformed tricuspid posterior annulus, wherein the fastener is selected from a suture that connects a septal end of the tricuspid posterior annulus to an anterior end of the tricuspid posterior annulus, or the deployed plication clip that is mounted onto the tricuspid posterior annulus; and
   (v) detaching the deployed plication clip from the delivery catheter, leaving the suture or deployed plication clip in place on the plicated tricuspid posterior annulus, and withdrawing the delivery catheter.

2. The method of claim 1, wherein the plication clip comprises a third elongate clip arm attached to the connector element.

3. The method of claim 1, wherein the plication clip comprises a tissue hook for capturing the posterior leaflet complex and disposing the posterior leaflet complex within the open position of the at least two elongate clip arms.

4. The method of claim 1, wherein the two elongate clip arms each comprise a check knob structure at a distal end.

5. The method of claim 1, wherein at least one of the two elongate clip arms is configured to bend into a hook shape.

6. The method of claim 1, wherein the connector element comprises one or more access ports for a catheter delivered positioning tool, and wherein the positioning tool engages one or more control wires disposed within the at least two elongate clip arms to actuate the plication clip to a closed position, to an open position, and to lock the plication clip in a closed position.

7. The method of claim 1, wherein the at least two elongate clip arms are at least partially covered with fabric.

8. The method of claim 1, wherein the step of actuating the plication clip comprises rotating the deployed plication clip that has captured the tricuspid posterior annulus.

9. The method of claim 1, further comprising the step of tethering the plication clip within the right ventricle.

10. The method of claim 1, wherein the steerable delivery catheter is directed to the tricuspid posterior annulus by tracking the steerable delivery catheter over a pre-positioned guide wire that is percutaneously inserted into the patient at a venous access site and advanced to the tricuspid posterior annulus.

11. The method of claim 1, wherein the step (iv) of securing comprises the step of imaging the heart using contrast media, ultrasound or X-ray to verify the position of the deployed plication clip and the deformation of the tricuspid valve into a bicuspidized tricuspid valve.

12. The method of claim 1, wherein the step (iv) of securing comprises the steps of imaging the heart using contrast media, ultrasound or X-ray to verify the position of the deployed plication clip and the deformation of the tricuspid valve into a bicuspidized tricuspid valve, and adjusting plication distance of the deployed plication clip by pulling a tether or tensile member attached to the plication clip to further reduce the annular diameter of the deformed tricuspid valve.

\* \* \* \* \*